(12) United States Patent
Thompson et al.

(10) Patent No.: US 12,011,255 B2
(45) Date of Patent: Jun. 18, 2024

(54) CATHETER TRACKING AND PLACEMENT SYSTEM INCLUDING LIGHT EMITTING DIODE ARRAY

(71) Applicant: Bard Access Systems, Inc., Salt Lake City, UT (US)

(72) Inventors: Chase Thompson, Bountiful, UT (US); Jerry Zhao, Salt Lake City, UT (US); Clark Knudsen, Salt Lake City, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 236 days.

(21) Appl. No.: 16/926,454

(22) Filed: Jul. 10, 2020

(65) Prior Publication Data
US 2021/0007626 A1    Jan. 14, 2021

Related U.S. Application Data

(60) Provisional application No. 62/873,778, filed on Jul. 12, 2019.

(51) Int. Cl.
*A61B 5/06* (2006.01)
*A61B 5/00* (2006.01)
(Continued)

(52) U.S. Cl.
CPC ............ *A61B 5/062* (2013.01); *A61B 5/6801* (2013.01); *A61B 5/7435* (2013.01); *A61B 90/36* (2016.02);
(Continued)

(58) Field of Classification Search
CPC .... A61B 2034/2051; A61B 2034/2072; A61B 2090/0807; A61B 2090/372;
(Continued)

(56) References Cited

U.S. PATENT DOCUMENTS 6,138,681 A     10/2000   Chen et al.
6,690,964 B2 *  2/2004    Bieger ................... A61B 34/20
                                              600/407

(Continued)

FOREIGN PATENT DOCUMENTS

EP          1698266 B1      6/2010
WO          2021011411      1/2021

OTHER PUBLICATIONS

PCT/US2020/41700 filed Jul. 10, 2020 International Search Report and Written Opinion dated Nov. 20, 2020.
(Continued)

*Primary Examiner* — Michael T Rozanski
(74) *Attorney, Agent, or Firm* — Rutan & Tucker LLP

(57) ABSTRACT

A tracking system configured to track the movement of the medical device. The medical device can include a proximal portion that has a magnetic element attached thereto. The system can include a console with a display, and a TLS sensor. The TLS sensor can be disposed on a surface of the patient and can include an LED array. The LED array can indicate a proximity of the medical device to the TLS sensor. The LED array can provide different colors and/or project images to display information regarding the location, orientation, distance, or depth of the medical device. The display can be disposed on an upper surface of the TLS sensor and can be configured to show an image of the medical device disposed therebelow, along with additional information and imagery, thus providing a standalone unit.

7 Claims, 9 Drawing Sheets

(51) Int. Cl.
*A61B 6/00* (2006.01)
*A61B 90/00* (2016.01)

(52) U.S. Cl.
CPC . *A61B 2090/374* (2016.02); *A61B 2090/3762* (2016.02); *A61B 2090/378* (2016.02); *A61B 2562/046* (2013.01)

(58) Field of Classification Search
CPC ...... A61B 2090/374; A61B 2090/3762; A61B 2090/378; A61B 2562/046; A61B 34/20; A61B 5/062; A61B 5/6801; A61B 5/7435; A61B 90/36; A61B 90/37
See application file for complete search history.

(56) References Cited

U.S. PATENT DOCUMENTS

| | | | |
|---|---|---|---|
| 8,388,541 | B2 | 3/2013 | Messerly et al. |
| 8,781,555 | B2 | 7/2014 | Burnside et al. |
| 8,849,382 | B2 | 9/2014 | Cox et al. |
| 9,456,766 | B2 | 10/2016 | Cox et al. |
| 9,492,097 | B2 | 11/2016 | Wilkes et al. |
| 9,521,961 | B2 | 12/2016 | Silverstein et al. |
| 9,526,440 | B2 | 12/2016 | Burnside et al. |
| 9,549,685 | B2 | 1/2017 | Cox et al. |
| 9,554,716 | B2 | 1/2017 | Burnside et al. |
| 9,636,031 | B2 | 5/2017 | Cox |
| 9,649,048 | B2 | 5/2017 | Cox et al. |
| 9,681,823 | B2 | 6/2017 | Messerly et al. |
| 9,999,371 | B2 | 6/2018 | Messerly et al. |
| 10,105,121 | B2 | 10/2018 | Burnside et al. |
| 10,165,962 | B2 | 1/2019 | Messerly et al. |
| 10,231,753 | B2 | 3/2019 | Burnside et al. |
| 10,238,418 | B2 | 3/2019 | Cox et al. |
| 10,342,575 | B2 | 7/2019 | Cox et al. |
| 10,449,330 | B2 | 10/2019 | Newman et al. |
| 10,524,691 | B2 | 1/2020 | Newman et al. |
| 10,602,958 | B2 | 3/2020 | Silverstein et al. |
| 10,751,509 | B2 | 8/2020 | Misener |
| 2008/0097475 | A1 | 4/2008 | Jaggi et al. |
| 2009/0001569 | A1 | 6/2009 | Messerly et al. |
| 2009/0002343 | A1 | 9/2009 | Cox et al. |
| 2010/0000362 | A1 | 2/2010 | Cox et al. |
| 2010/0094116 | A1 | 4/2010 | Silverstein |
| 2010/0002045 | A1 | 8/2010 | Burnside et al. |
| 2011/0000155 | A1 | 1/2011 | Cox et al. |
| 2011/0166442 | A1 | 7/2011 | Sarvazyan |
| 2011/0002821 | A1 | 11/2011 | Burnside et al. |
| 2011/0002951 | A1 | 12/2011 | Cox et al. |
| 2012/0001430 | A1 | 6/2012 | Silverstein et al. |
| 2012/0002208 | A1 | 8/2012 | Messerly et al. |
| 2013/0000061 | A1 | 1/2013 | Wilkes et al. |
| 2013/0000601 | A1 | 3/2013 | Messerly et al. |
| 2013/0002454 | A1 | 9/2013 | Messerly et al. |
| 2014/0000316 | A1 | 1/2014 | Newman et al. |
| 2014/0000462 | A1 | 2/2014 | Newman et al. |
| 2014/0001074 | A1 | 4/2014 | Cox et al. |
| 2014/0001881 | A1 | 7/2014 | Misener |
| 2014/0003034 | A1 | 10/2014 | Burnside et al. |
| 2014/0296694 | A1 | 10/2014 | Jaworski |
| 2015/0000187 | A1 | 1/2015 | Cox et al. |
| 2015/0012077 | A1 | 1/2015 | Parker et al. |
| 2015/0002971 | A1 | 10/2015 | Cox et al. |
| 2016/0287134 | A1 | 10/2016 | Foong et al. |
| 2017/0000205 | A1 | 1/2017 | Cox et al. |
| 2017/0000795 | A1 | 3/2017 | Silverstein et al. |
| 2017/0000796 | A1 | 3/2017 | Burnside et al. |
| 2017/0079548 | A1 | 3/2017 | Silverstein et al. |
| 2017/0002317 | A1 | 8/2017 | Cox et al. |
| 2017/0002810 | A1 | 10/2017 | Messerly et al. |
| 2018/0042517 | A1 | 2/2018 | van der Weide et al. |
| 2018/0001165 | A1 | 5/2018 | Newman et al. |
| 2018/0002961 | A1 | 10/2018 | Messerly et al. |
| 2019/0000698 | A1 | 3/2019 | Burnside et al. |
| 2019/0000991 | A1 | 4/2019 | Messerly et al. |
| 2020/0000548 | A1 | 2/2020 | Newman et al. |
| 2020/0001383 | A1 | 5/2020 | Newman et al. |
| 2020/0002372 | A1 | 7/2020 | Silverstein et al. |

OTHER PUBLICATIONS

PCT/US2020/41700 filed Jul. 10, 2020 International Preliminary Report on Patentability dated Jan. 18, 2022.
EP 20841590.1 filed Feb. 4, 2022 Extended European Search Report dated May 25, 2023.

\* cited by examiner

CATHETER TRACKING AND PLACEMENT SYSTEM INCLUDING LIGHT EMITTING DIODE ARRAY

PRIORITY

This application claims the benefit of priority to U.S. Provisional Application No. 62/873,778, filed Jul. 12, 2019, which is incorporated in its entirety into this application.

BACKGROUND

Most catheter placement devices require various medical devices coupled with separate stand-alone display devices, showing information or overlay imaging of the medical device location. Inevitably the display devices are positioned away from the medical device location and the patient, and requires the user to divide their time between medical device insertion location and the display device. This is of particular relevance with medical device tracking systems that require the user to both manipulate one or more medical devices at an insertion site on a patient as well as provide consistent attention to a display device positioned elsewhere. What is needed, therefore is a system and a method of tip location devices located on or near the patient and indicates to a user the location of a medical device that is within a patient.

SUMMARY

Briefly summarized, embodiments disclosed herein are directed to a tracking system configured to track the movement of the medical device. The system includes a tip location system ("TLS") sensor that includes an LED array. The LED array can indicate a proximity of the medical device to the TLS sensor. The LED array can provide different colors or project images to display information regarding the location, orientation, distance, or depth of the medical device. In embodiments, a display is disposed on an upper surface of the TLS sensor and is configured to show an image of the medical device disposed therebelow, along with additional information and imagery.

In an aspect of the invention, a medical device tracking system is disclosed, comprising a tracking circuit designed to track movement of a medical device in a body, the tracking circuit including a reception component designed to detect a magnetic field associated with the medical device and to generate magnetic field strength data; and a processor designed to iteratively compute position data of the medical device according to the magnetic field strength data; and a sensor disposed on a skin surface of the patient, the sensor including a light emitting diode (LED) array, the LED array including one or more LED lights, the LED array indicating a proximity of the medical device to the sensor.

In some embodiments, the LED array includes a first LED light disposed proximate a first side of the sensor, a second LED light disposed proximate a second side of the sensor, and a third LED light disposed proximate a central portion of the sensor, and wherein one LED light of the first, second, and third LED lights illuminates when the medical device is proximate thereto. The one-or-more LED lights of the LED array display more than one color. The more-than-one color indicates one of a distance or a depth of the medical device relative to the sensor. The LED array includes a matrix of LED lights disposed on an upper surface of the sensor.

Also disclosed is a tracking system for tracking a medical device, the medical device including a magnetic element attached to a distal portion thereof, the system comprising a sensor configured to track movement of the medical device. The sensor comprises a reception component configured to detect a magnetic field associated with the magnetic element and to generate magnetic field strength data, a processor designed to iteratively compute position data of the distal portion of the medical device according to the magnetic field strength data, and to simulate insertion of the distal portion of the medical device into a body of a patient. The system includes a display disposed on an upper surface of the sensor. The display is configured to depict an image from the computed position data of the distal portion of the medical device.

In some embodiments, the display depicts a symbol to indicate one of a location, an orientation, a distance, or a depth of the medical device when the medical device is proximate to the sensor. The display depicts an image of the medical device when the medical device is disposed below the sensor. The symbol includes one of an alphanumeric symbol, an image, or an icon. The display further depicts one of additional information or imaging of the patient, to provide an augmented view of the medical device within the patient and disposed below the sensor. The imaging of the patient includes one of an x-ray, an ultrasound, a PET, a CT, or an MM image of the patient. The imaging of the patient is modified in accordance with a position of the sensor on the patient to correspond the imaging with a portion of the patient disposed below the sensor.

Also disclosed is a method of tracking a medical device, comprising positioning a sensor on a target area of a patient, the sensor including an LED array of one or more LED lights, inserting a medical device in a vasculature of the patient, and indicating a proximity of the medical device to the sensor by illuminating the one-or-more LED lights of the LED array.

In some embodiments, the proximity of the medical device to the sensor includes one of a distance or a depth of the medical device in three-dimensional space. The one-or-more LED lights of the LED array display more than one color, the more-than-one color indicating the proximity of the medical device relative to the sensor. The one-or-more LED lights of the LED array illuminate when the medical device is disposed directly thereunder. The one-or-more LED lights of the LED array project a symbol onto a surface of the patient indicating one of a location, a direction, a distance, or a depth of the medical device relative the sensor. The symbol includes one of an alphanumeric symbol, an image, or an icon. The LED array is a display configured to provide an image of the medical device when the medical device is disposed below the sensor.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION

Figure 1:
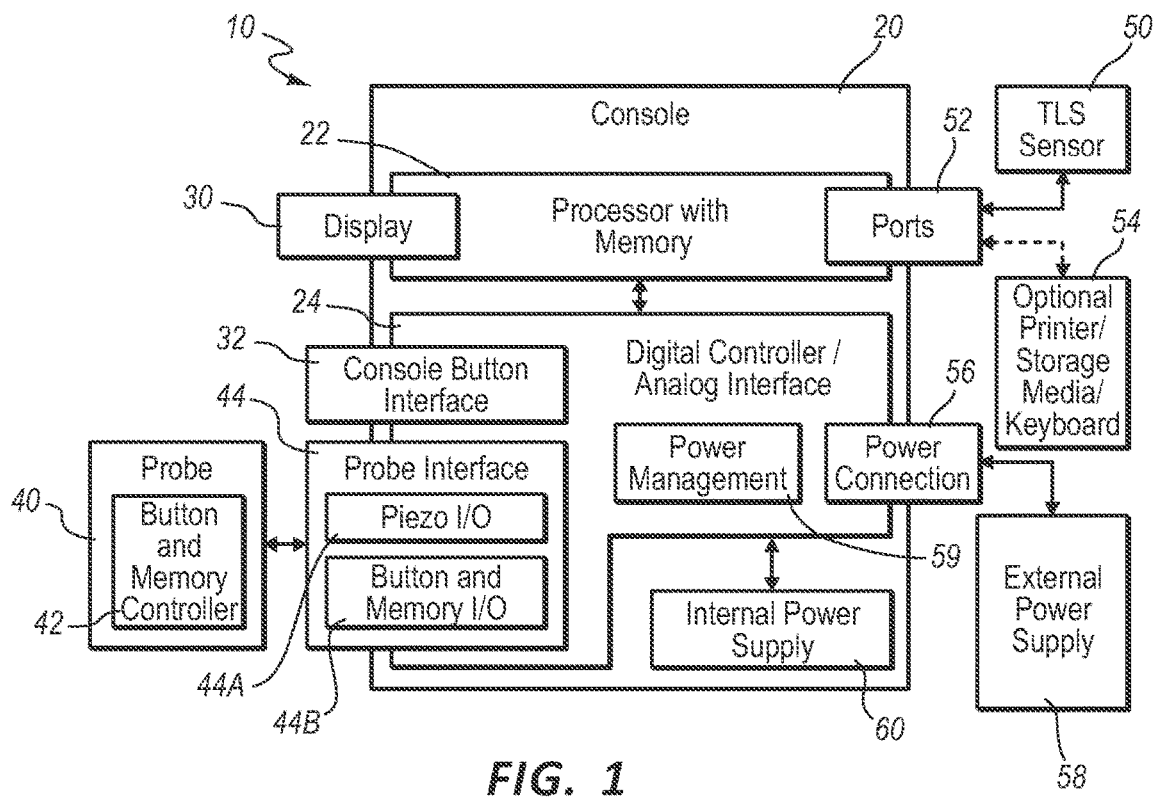
FIG. 1 is a block diagram depicting various elements of an integrated system for intravascular placement of a catheter, according to one example embodiment.

Reference will now be made to figures wherein like structures will be provided with like reference designations. It is understood that the drawings are diagrammatic and schematic representations of exemplary embodiments of the concepts provided herein, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

The terms "upper," "lower," "top," "bottom," "underside," "upperside" and the like, which also are used to describe the present system, are used in reference to the illustrated orientation of the embodiment. The terms "left" and "right" are used consistently throughout the disclosure and are used to describe structures from the perspective of the user or clinician using the device.

Assisted Catheter Placement

Embodiments are generally directed to a catheter placement system configured for accurately placing a catheter within the vasculature of a patient. In one embodiment, the catheter placement system employs at least two modalities for improving catheter placement accuracy: 1) ultrasound-assisted guidance for introducing the catheter into the patient's vasculature; and 2) a tip location/navigation system ("TLS"), or magnetically-based tracking of the catheter tip during its advancement through the tortuous vasculature path to detect and facilitate correction of any tip malposition during such advancement. The ultrasound guidance and tip location features of the present system according to one embodiment are integrated into a single device for use by a clinician placing the catheter. Integration of these two modalities into a single device simplifies the catheter placement process and results in relatively faster catheter placements. For instance, the integrated catheter placement system enables ultrasound and TLS activities to be viewed from a single display of the integrated system. Also, controls located on an ultrasound probe or the TLS sensor of the integrated device, which are maintained within the sterile field of the patient during catheter placement, can be used to control functionality of the system, thus precluding the need for a clinician to reach out of the sterile field in order to control the system.

In another embodiment, a third modality, i.e., ECG signal-based catheter tip guidance, is included in the integrated system to enable guidance of the catheter tip to a desired position with respect to a node of the patient's heart from which the ECG signals originate. Such ECG-based positional assistance is also referred to herein as "tip confirmation."

Combination of the three modalities above according to one embodiment enables the catheter placement system to facilitate catheter placement within the patient's vasculature with a relatively high level of accuracy, i.e., placement of the distal tip of the catheter in a predetermined and desired position. Moreover, because of the ECG-based guidance of the catheter tip, correct tip placement may be confirmed without the need for a confirmatory X-ray. This, in turn, reduces the patient's exposure to potentially harmful x-rays, the cost and time involved in transporting the patient to and from the x-ray department, costly and inconvenient catheter repositioning procedures, etc.

Figure 2:
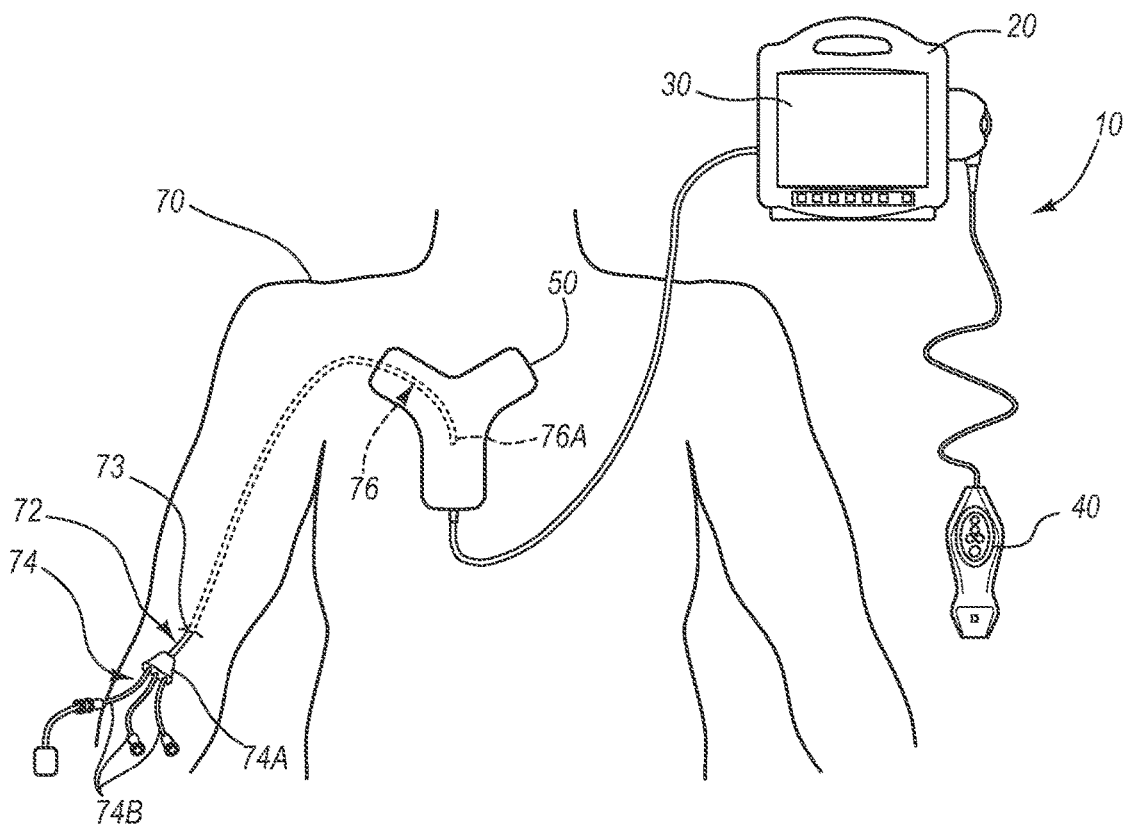
FIG. 2 is a simplified view of a patient and a catheter being inserted therein with assistance of the integrated system of FIG. 1.

Reference is first made to FIGS. 1 and 2 which depict various components of a catheter placement system ("system"), generally designated at 10, configured in accordance with one example embodiment. As shown, the system 10 generally includes a console 20, display 30, probe 40, and sensor 50, each of which is described in further detail below.

FIG. 2 shows the general relation of these components to a patient 70 during a procedure to place a catheter 72 into the patient vasculature through a skin insertion site 73. FIG. 2 shows that the catheter 72 generally includes a proximal portion 74 that remains exterior to the patient and a distal portion 76 that resides within the patient vasculature after placement is complete. The system 10 is employed to ultimately position a distal tip 76A of the catheter 72 in a desired position within the patient vasculature. In one embodiment, the desired position for the catheter distal tip 76A is proximate the patient's heart, such as in the lower one-third (⅓rd) portion of the Superior Vena Cava ("SVC"). Of course, the system 10 can be employed to place the catheter distal tip in other locations. The catheter proximal portion 74 further includes a hub 74A that provides fluid communication between the one or more lumens of the catheter 72 and one or more extension legs 74B extending proximally from the hub.

Figure 3:
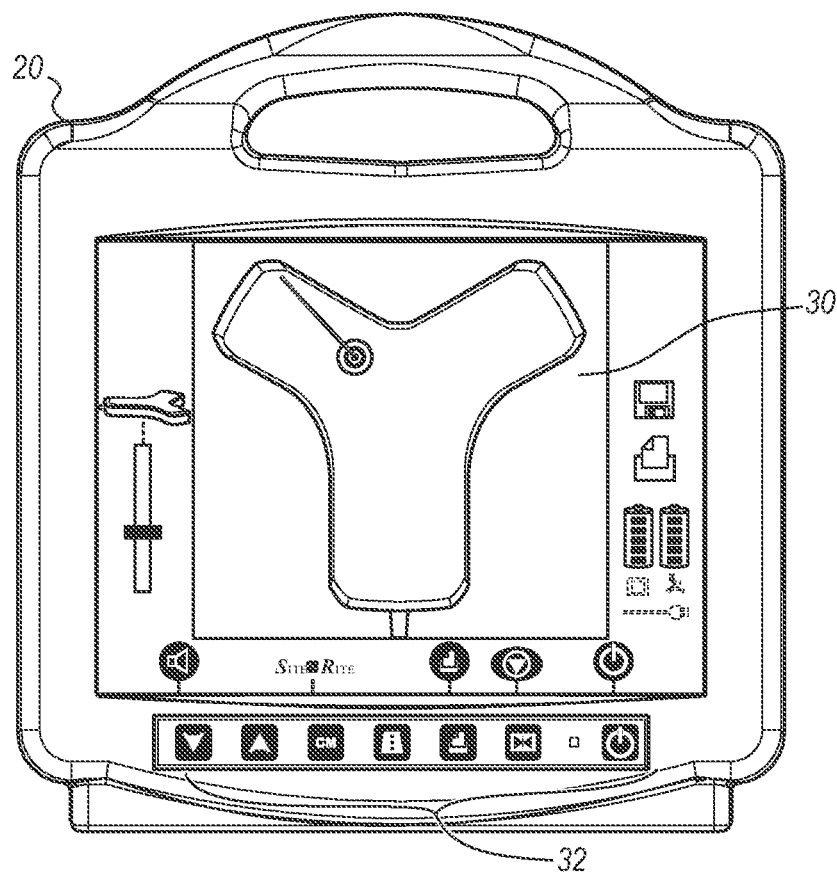
FIG. 3 is an exemplary console and display of the integrated system of FIG. 1.

An example implementation of the console 20 is shown in FIG. 3, though it is appreciated that the console can take one of a variety of forms. A processor 22, including non-volatile memory such as EEPROM for instance, is included in the console 20 for controlling system function during operation of the system 10, thus acting as a control processor. A digital controller/analog interface 24 is also included with the console 20 and is in communication with both the processor 22 and other system components to govern interfacing between the probe 40, sensor 50, and other system components.

The system 10 further includes ports 52 for connection with the sensor 50 and optional components 54 including a printer, storage media, keyboard, etc. The ports in one embodiment are USB ports, though other port types or a combination of port types can be used for this and the other interfaces connections described herein. A power connection 56 is included with the console 20 to enable operable connection to an external power supply 58. An internal battery 60 can also be employed, either with or exclusive of an external power supply. Power management circuitry 59 is included with the digital controller/analog interface 24 of the console to regulate power use and distribution.

The display 30 in the present embodiment is integrated into the console 20 and is used to display information to the clinician during the catheter placement procedure. In another embodiment, the display may be separate from the console. As will be seen, the content depicted by the display 30 changes according to which mode the catheter placement system is in: US, TLS, or in other embodiments, ECG tip confirmation. In one embodiment, a console button interface 32 (see FIGS. 1, 3) and buttons included on the probe 40, the TLS sensor 50, or combinations thereof, can be used to immediately call up a desired mode to the display 30 by the clinician to assist in the placement procedure. Further details of which are disclosed herein. In one embodiment, information from multiple modes, such as TLS and ECG, may be displayed simultaneously. Thus, the single display 30 of the system console 20 can be employed for ultrasound guidance in accessing a patient's vasculature, TLS guidance during catheter advancement through the vasculature, and (as in later embodiments) ECG-based confirmation of catheter distal tip placement with respect to a node of the patient's heart. In one embodiment, the display 30 is an LCD device. In one embodiment the display 30 is a touch screen device.

FIG. 1 shows that the probe 40 includes button and memory controller 42 for governing button and probe operation. The button and memory controller 42 can include non-volatile memory, such as EEPROM, in one embodiment. The button and memory controller 42 is in operable communication with a probe interface 44 of the console 20, which includes a piezo input/output component 44A for interfacing with the probe piezoelectric array and a button and memory input/output component 44B for interfacing with the button and memory controller 42.

Further details of the catheter placement system 10 can be found in U.S. Pat. Nos. 8,388,541; 8,781,555; 8,849,382; 9,521,961; 9,526,440; 9,549,685; 9,636,031; 9,649,048; 9,681,823; 9,999,371; 10,105,121; 10,165,962; 10,238,418; and 10,602,958, each of which is incorporated by reference in its entirety into this application.

TLS Sensor LED Array

Figure 4:
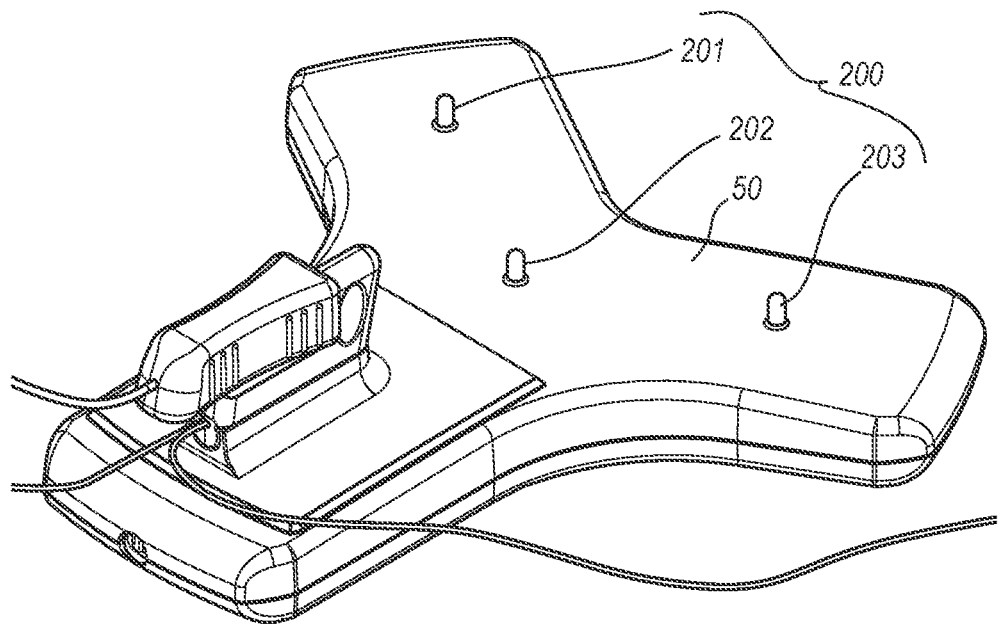
FIG. 4 is a perspective view of a sensor in accordance with an embodiment.

With reference to FIGS. 4-13 and in particular FIG. 4, in an embodiment, the TLS sensor ("sensor") 50 can include an LED array 200 comprising one or more individual LED lights, e.g. LED lights 201, 202, 203. The LED array 200 can be disposed on a surface of the sensor 50, for example an upper surface thereof. It will be appreciated, however, that one or more LED lights of the array 200 can be disposed on one or more surfaces of the sensor 50 for example a side surface thereof. In an embodiment, one or more LED lights of the array 200 can protrude from a surface of the sensor 50. In an embodiment, one or more LED lights of the array 200 are integrated with the sensor 50 so as to define a substantially continuous surface with the sensor 50. It will also be appreciated that other visual indicators can also be used in place of, or in conjunction with the LED array 200, for example tungsten bulbs, fluorescent bulbs, different colored tabs, or the like.

Figure 5:
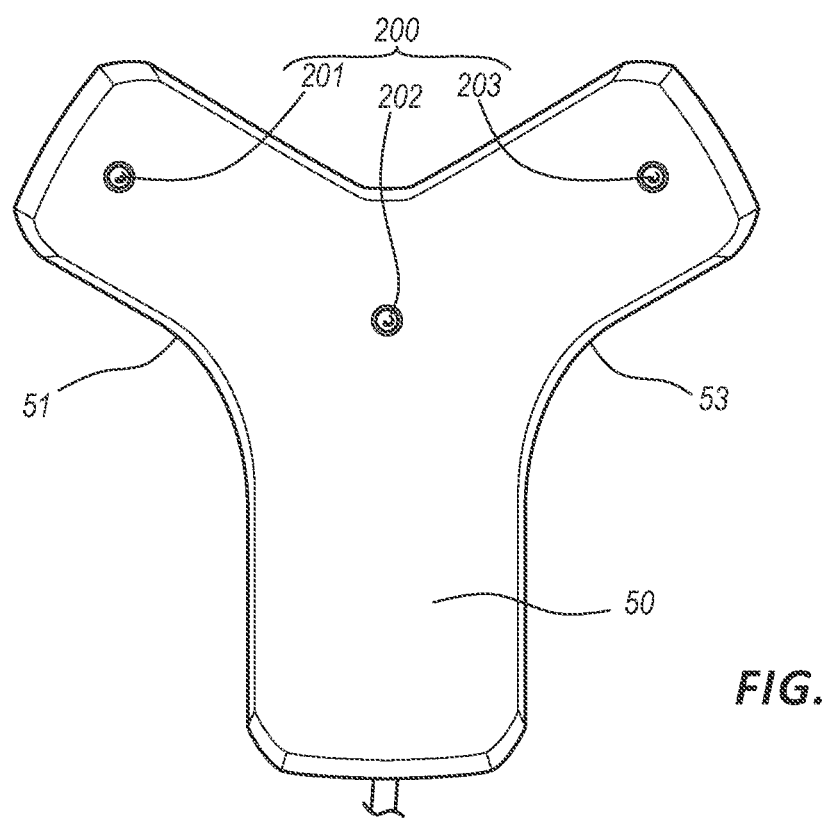
FIG. 5 is a first plan view of a sensor in accordance with an embodiment.
Figure 6:
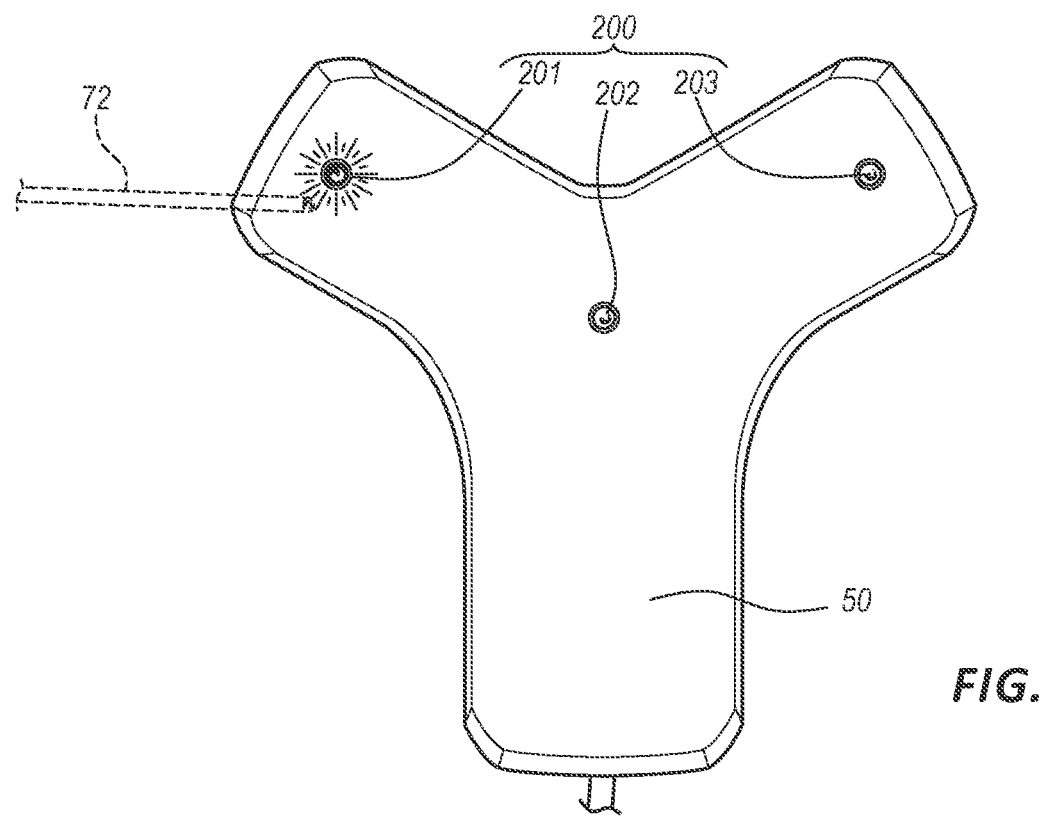
FIG. 6 is a second plan view of the sensor in accordance with the embodiment of FIG. 5.
Figure 7:
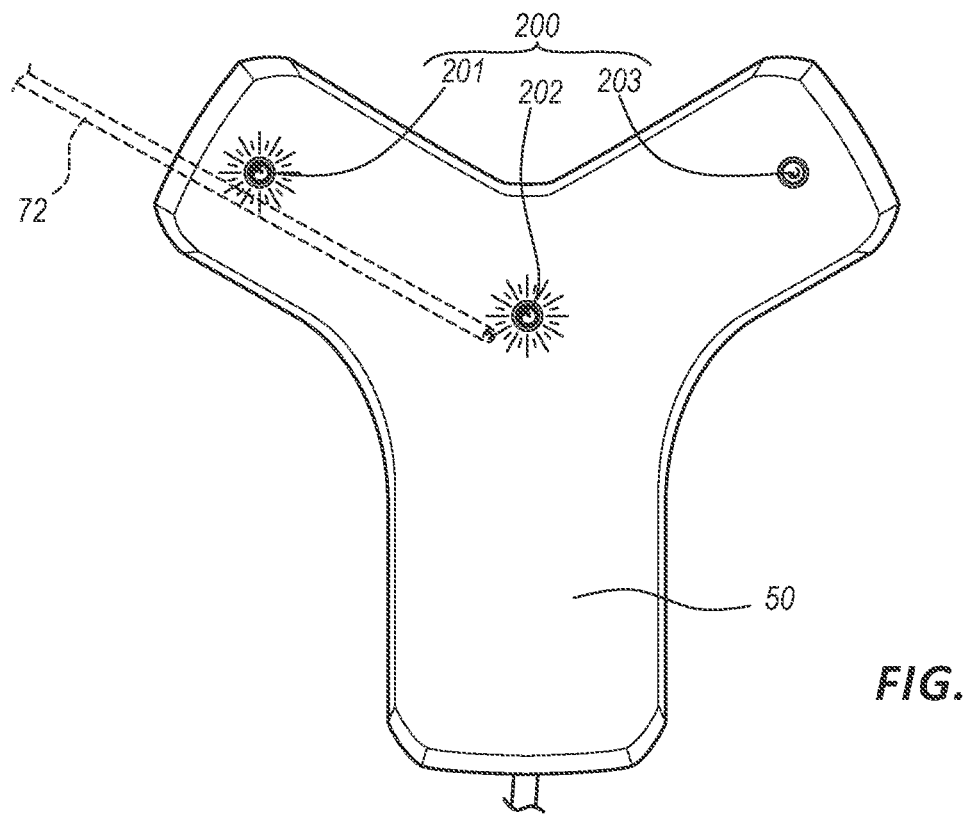
FIG. 7 is a third plan view of the sensor in accordance with the embodiment of FIG. 5.

In an embodiment, the LED array 200 can indicate a location of a medical device, for example catheter 72, relative to the sensor 50. FIGS. 5-8, show a sensor 50, including an LED array 200. As shown in FIG. 5 when no catheter 72 is proximate the sensor 50, none of the LED lights of the LED array 200 are illuminated. As shown in FIG. 6 when the catheter 72 is proximate a first side 51 of sensor 50, then a first LED light 201, most proximate the catheter 72, is illuminated and the remaining LED lights 202, 203 of the LED array 200 are not. Similarly, when the catheter 72 is proximate a second side 53 of sensor 50, then a second LED light 203, most proximate the catheter 72, is illuminated and the remaining LED lights 201, 202 of the LED array 200 are not. As shown in FIG. 7, as a catheter 72 is moved further towards the sensor 50, and a target area substantially at LED light 202, additional LED lights 201, 202 of the array 200 can also illuminate.

In an embodiment, one or more LED lights 201, 202, 203 of the array 200 can display more than one colors to provide a two-dimensional indication, compared with a one dimensional, or binary (on/off), indication. For example, each of the LED lights 201, 202, 203 of the array 200 can display a green, yellow, and red color. The color change can indicate a proximity of the catheter 72 relative to each of the LED lights 201, 202, 203 of the array 200. By interpreting the different color change in the individual LED lights 201, 202, 203 of the array 200 a user can determine the position of the catheter 72 relative to the sensor 50.

Figure 8:
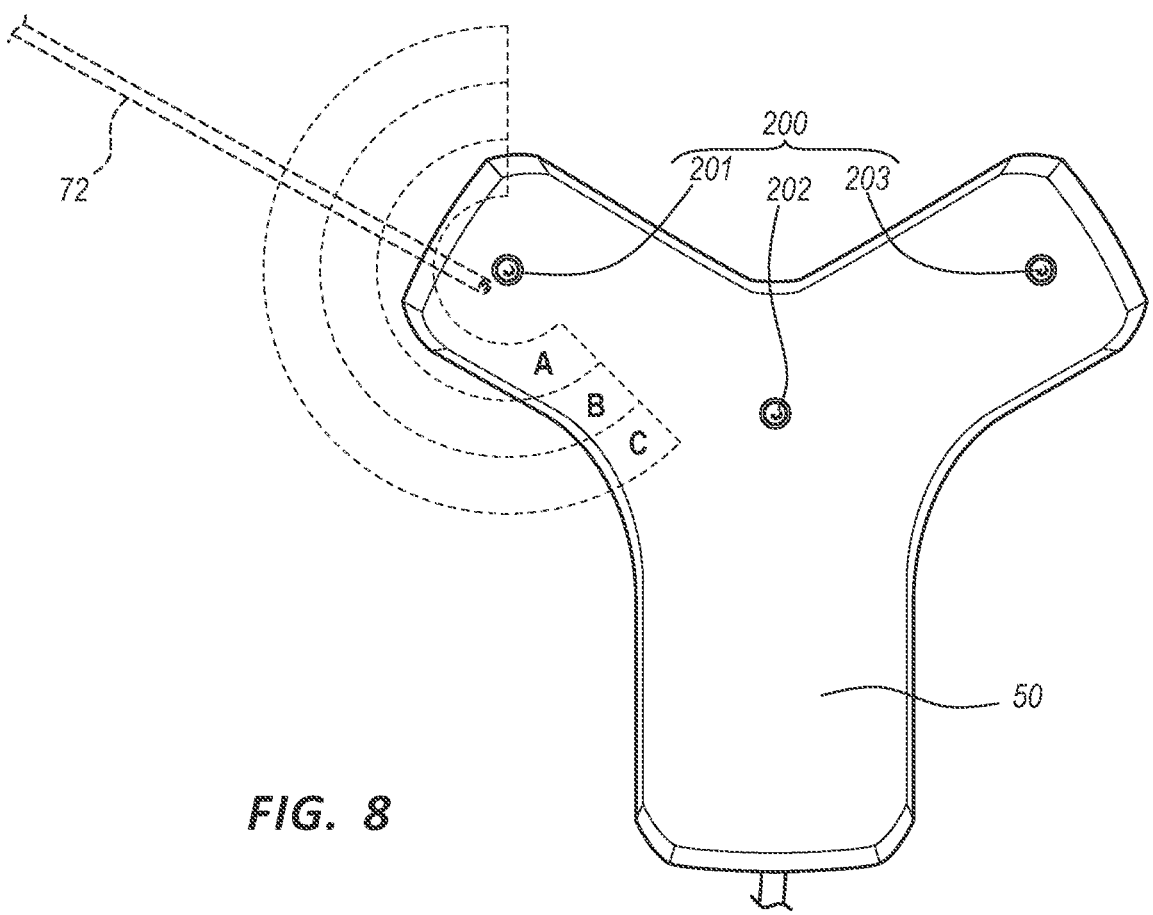
FIG. 8 is a fourth plan view of the sensor in accordance with the embodiment of FIG. 5.
Figure 9:
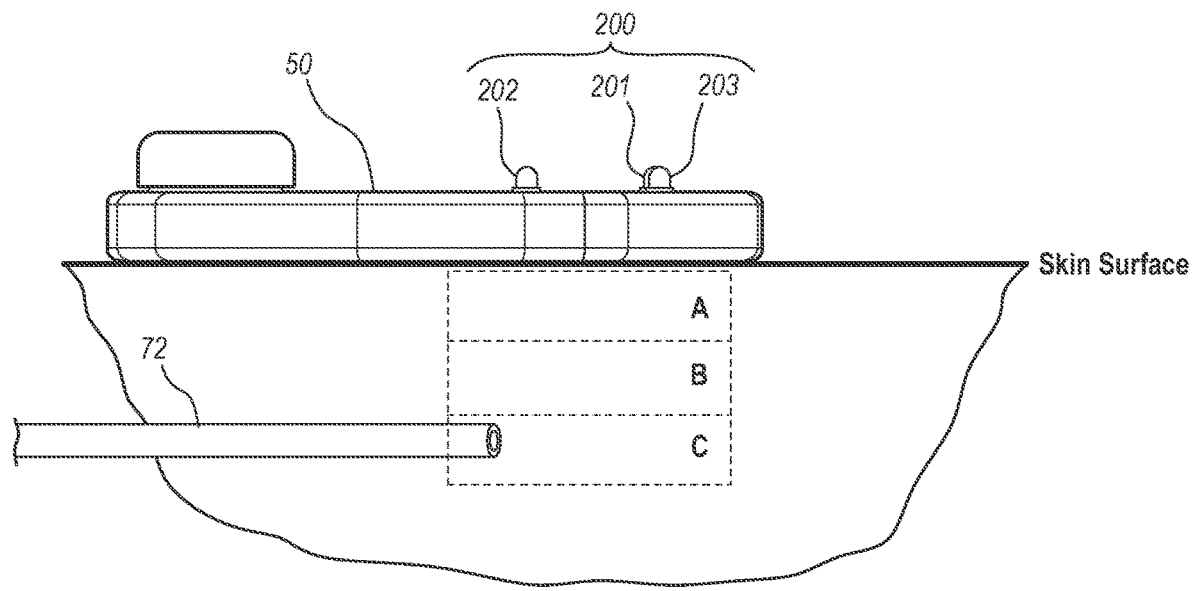
FIG. 9 is a first side view of a sensor in accordance with an embodiment.
Figure 10:
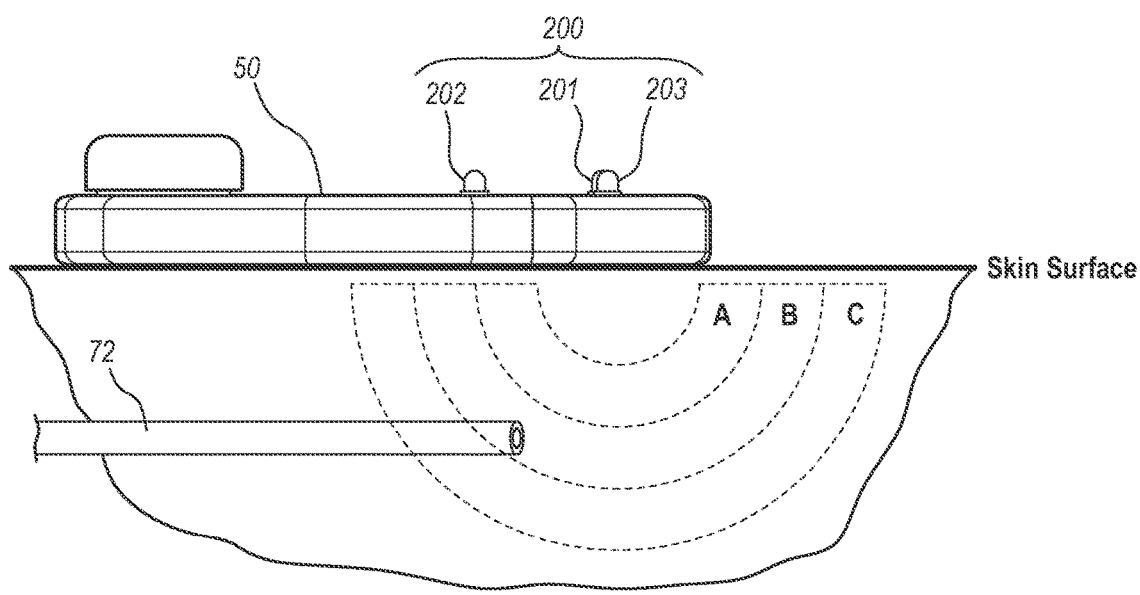
FIG. 10 is a second side view of the sensor in accordance with the embodiment of FIG. 9.

As shown in FIG. 8, in an embodiment, the color change can indicate a proximity of the catheter 72 relative to sensor 50 along a horizontal plane, substantially parallel to a skin surface of the patient 70 on which the sensor 50 is disposed. For example, when the catheter 72 is within a proximity of the sensor 50 substantially defined by zone A, the LED light 201 can display a green color. When the catheter 72 is within zone B the LED light 201 can display a yellow color and when in zone C a red color. In an embodiment, as shown in FIG. 9 the color change can indicate a depth of the catheter 72 relative to sensor 50 along a vertical plane, substantially normal to a skin surface of the patient 70 on which the sensor 50 is disposed. In an embodiment, as shown in FIG. 10 the color change can indicate a proximity of the catheter 72 relative to sensor 50 within a three-dimensional spherical space of each LED light of the array 200.

It will be appreciated that any number and order of the zones, absolute spacing of the zones, types of colors displayed, and specific information represented by each color can vary without departing from the spirit of the invention. In an embodiment, each zone can denote a 5 cm spacing, for example, zone A is when the catheter 72 is <5 cm from the sensor 50, zone B is when the catheter 72 is between 5 cm and 10 cm from the sensor 50, and zone C is when the catheter 72 is between 10 cm and 15 cm from the sensor 50. Although it will be appreciated that each zone can denote different absolute distance ranges. In an embodiment a continuum of color variation can indicate and continuum of change in distance, depth, or combinations thereof.

Figure 11:
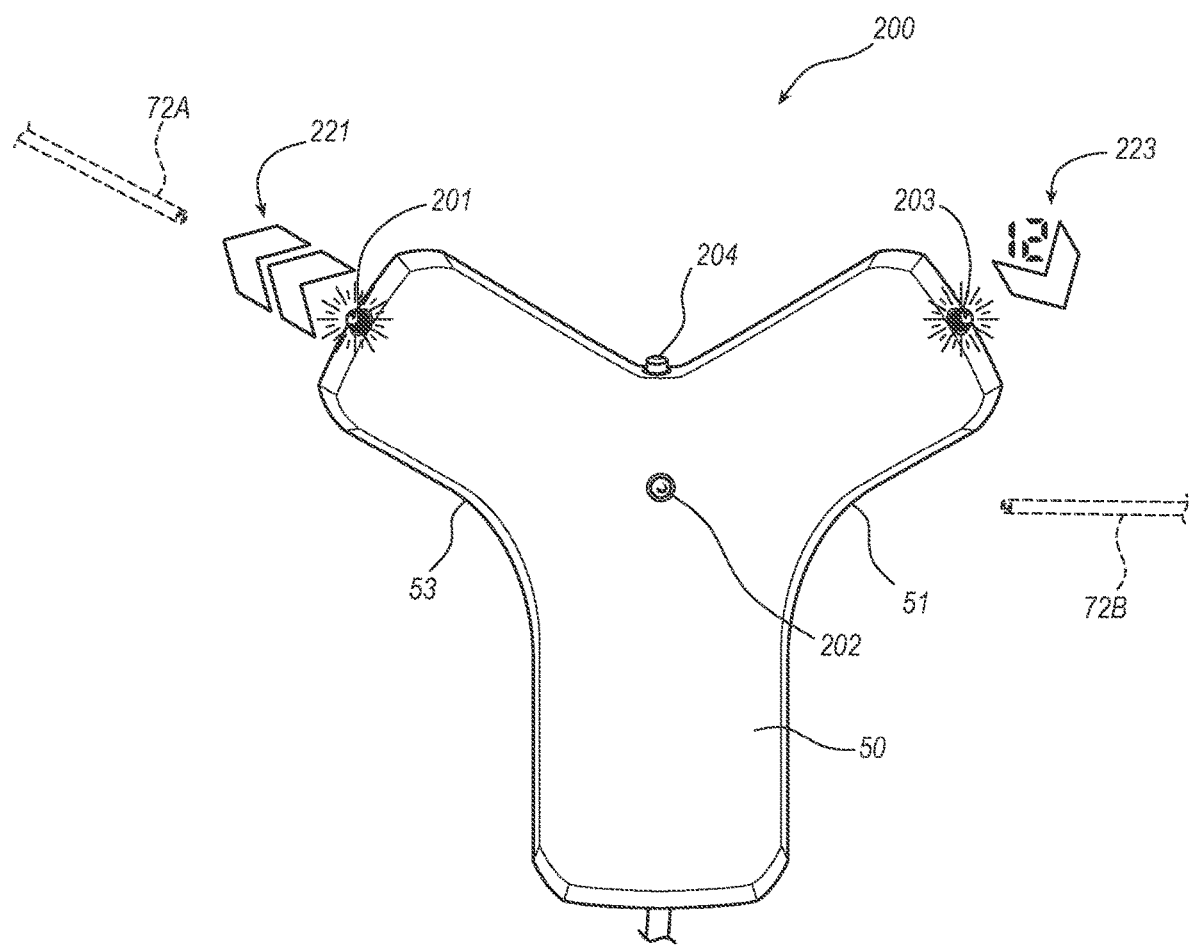
FIG. 11 is a plan view of a sensor in accordance with an embodiment.

In an embodiment, as shown in FIG. 11, one or more LED lights of the array 200, e.g. LED lights 201, 203, 204, can project a symbol, for example an image, alphanumerical symbol, or the like. The symbol can be projected on to a surface of the patient 70, proximate the sensor 50. The symbol can indicate a location, distance, depth, combinations thereof, or similar information regarding the catheter 72 relative to the sensor 50. For example, when a catheter position 72A is proximate a first side of the sensor 50, a first LED light 201 of the array can project a symbol 221 of arrows onto a surface of the patient 70, the angle of the arrow can indicate a direction of the catheter 72 relative to the sensor 50, the number of arrows can indicate a distance of the catheter 72 relative to the sensor 50 and a color can indicate a depth of the catheter 72 relative to the sensor 50. As a further example, also shown in FIG. 11, a second catheter position 72B is shown proximate a second side with a symbol 223 projected on to a surface of the patient 70 indicating a location and distance, further a color can indicate depth. It will be appreciated that for the remaining LED lights of the LED array 200 where no medical device is proximate, e.g. LED light 204, then no symbol will be projected.

Accordingly, each of the LED lights of the array 200 can indicate a location, direction, distance, depth of a catheter 72 relative to the sensor 50. It will be appreciated that any combination of shapes, symbols, alphanumeric symbols, colors, and the like can be used to indicate any combination of location, direction, orientation, distance, or depth of the catheter 72 relative to the sensor 50 without departing from the spirit of the invention. Further it will be appreciated that the position of more than one medical device can be displayed by the LED array 200.

Advantageously, the LED lights 201, 202, 203 of the array 200 included with the sensor 50 provide a visual indication of the location of the inserted medical device, catheter 72. Accordingly, the visual indication is provided to the user without requiring a separate console 20 and display 30, thereby providing a lower cost system. Alternatively, with the visual indication provided by the sensor 50, such information is no longer required to be displayed on the display 30, thereby freeing up display real estate. This provides a cleaner, less confusing interface on the display 30, or allows for different information to be provided, or allows for a smaller, more compact display, or combinations thereof. Further, a user does not have to divert their attention away from the patient 70, and insertion site, in order to determine if a distal tip 76A of the catheter 72 is approaching a target location. A user can determine a location of the distal tip 76a of the catheter 72 while manipulating the proximal portion 74 without having to divert their attention to a display 30, located remotely.

In an embodiment the sensor 50 can be used to track the location of the distal tip of the catheter as the catheter is advanced. The sensor can be moved along with the tip so a user can track its location within the body. Since the location of the medical device is measured as a relative distance between the medical device and the sensor 50, the sensor 50 can also be moved along with, or a head of, the medical device as it is advanced within the vasculature of the patient 70. The LED array 200 can indicate to a user where to move the sensor 50 across a surface of the patient 70 in order to maintain proximity with the distal tip 76A disposed within the patient 70. Accordingly, the user can visually determine a location of the medical device as it is advanced.

Figure 12:
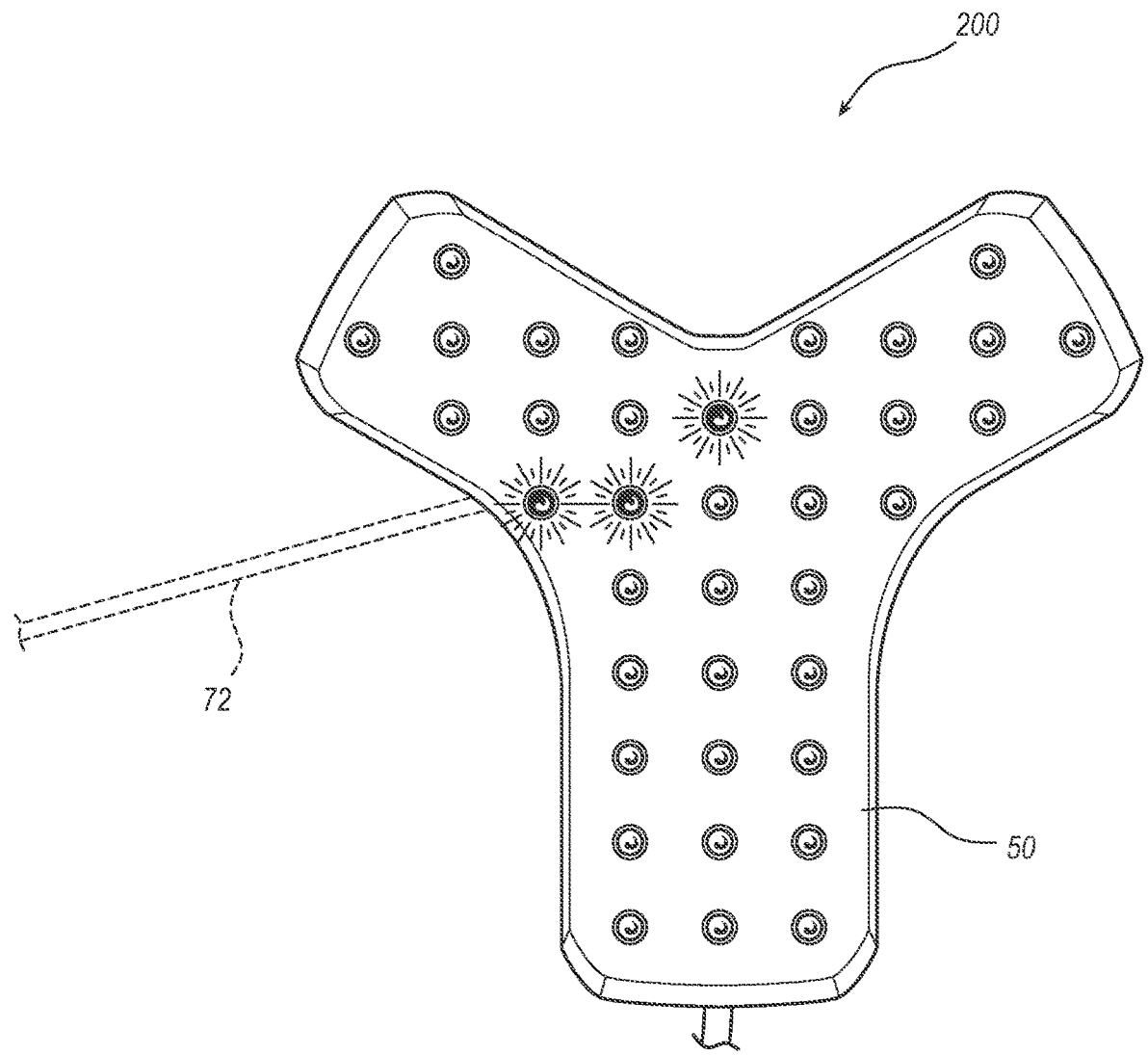
FIG. 12 is a plan view of a sensor in accordance with an embodiment.

In an embodiment, the density of LED lights within the array 200 can vary from what is shown in FIGS. 5-11. As shown in FIG. 12, in an embodiment, the array 200 can include a plurality of LED lights arranged in a matrix across one or more surfaces of the sensor 50. In an embodiment, the LED array 200 can cover substantially the entire surface of the sensor 50. As the density of LED lights within the array 200 increases, the detection zone area associated with each LED light of the array 200 decreases. As such, the resolution of the catheter location, orientation, etc. can be increased. For example, as shown in FIG. 12 the density of lights in the array 200 allows only the LED lights immediately above the catheter 72 to illuminate. This provides greater detail as to the location and orientation of the catheter 72 with respect to the sensor 50.

Figure 13:
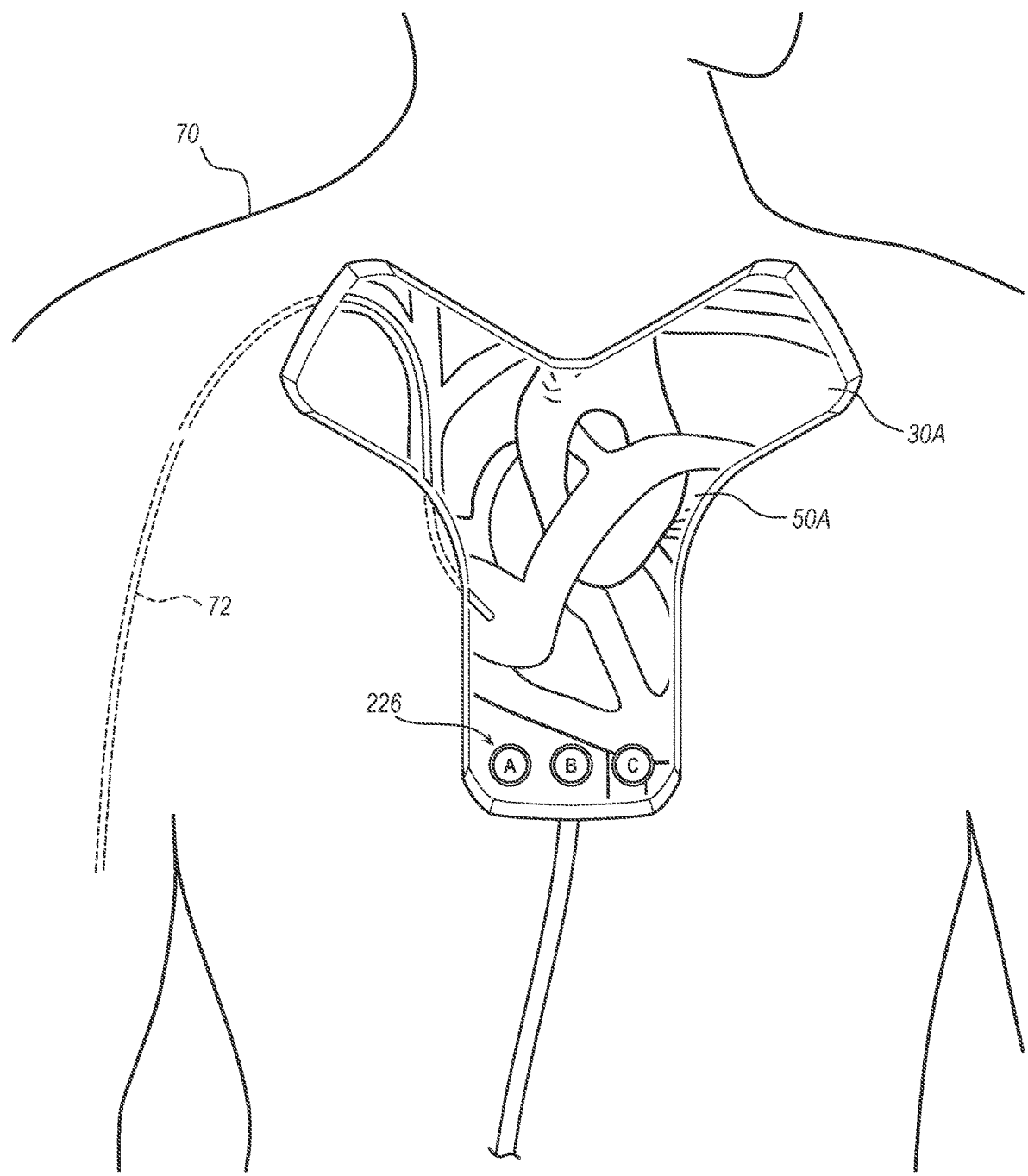
FIG. 13 is a first plan view of a sensor in accordance with an embodiment.
Figure 14:
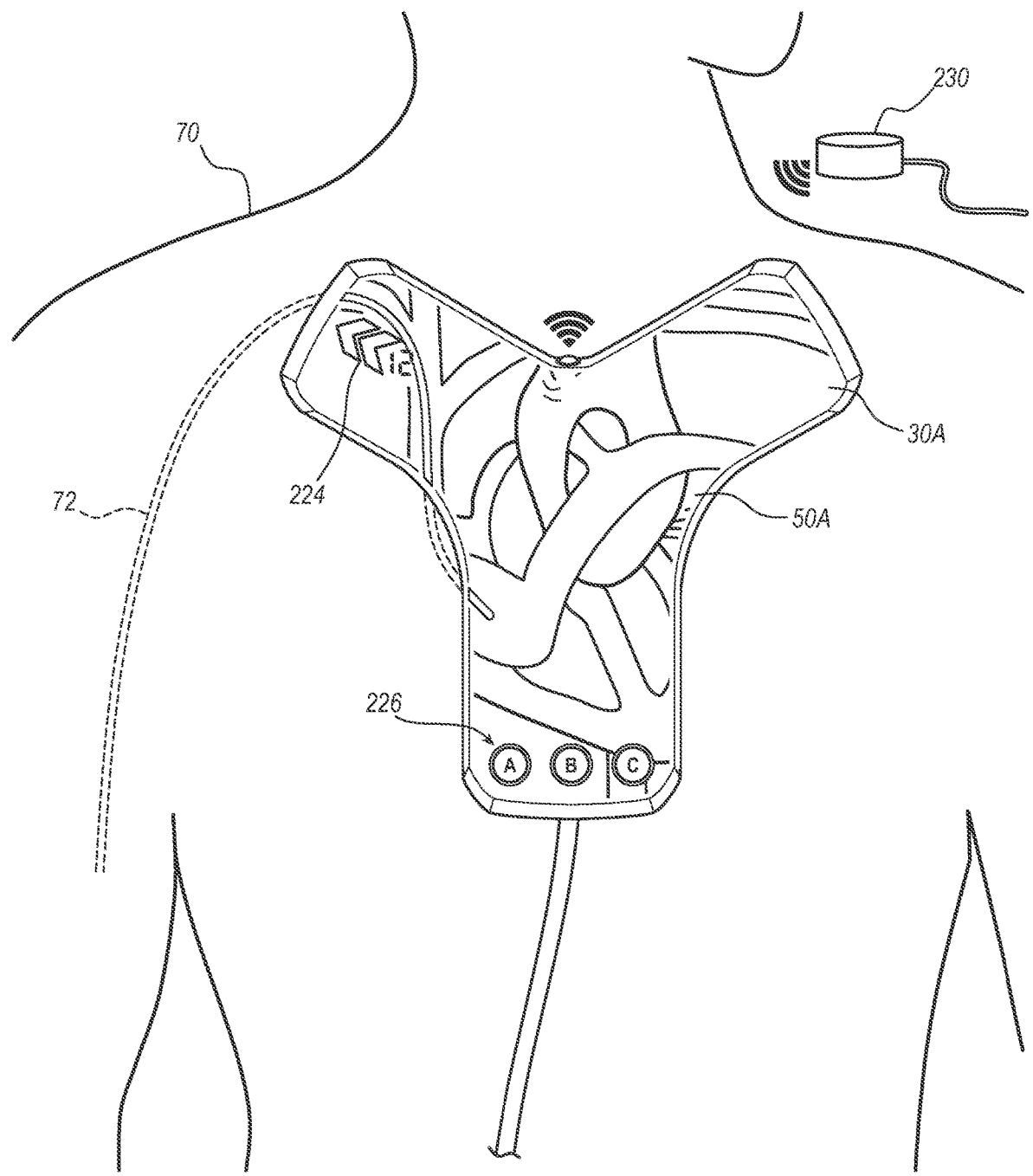
FIG. 14 is a second plan view of the sensor in accordance with the embodiment of FIG. 13.

As shown in FIGS. 13-14, in an embodiment, the functionality of the console 20 and display 30 can be included within the sensor 50 to provide a system 10 substantially included as a single-unit system 50A. A surface of the system 50A can include a display 30A similar to display 30. Further, it will be appreciated that the medical device, catheter 72 or the like, can be communicatively coupled with the system 50A by either wired or wireless communication modes. In an embodiment, the system 50A can be further coupled with additional devices such as virtual reality headsets, augmented reality glasses and the like to further display imaging and information to the user.

Display 30A can show an image of the catheter 72 disposed therebelow, within the patient 70. Further, additional imaging and information of the patient 70 can also be shown on display 30A to provide an augmented view of the medical device within the patient 70, disposed below system 50A and the sensor thereof. It will be appreciated that the imaging and information of the patient 70 can include x-ray, Ultrasound, PET, CT, MRI images, combinations thereof, or the like.

In an embodiment, the system 50A is configured to transform the imaging and information, into objects of three-dimensionally rendered virtual anatomy with a virtualization algorithm. Further details of three-dimensional rendering of images can be found in U.S. Publication No. 2019/0167148; U.S. Publication No. 2019/0223757; and U.S. Publication No. 2019/0307419, each of which is incorporated by reference in its entirety into this application. The display 30A is configured to display both the image of the medical device and the objects of virtual anatomy that correspond to portions of the patient disposed below the system 50A. The imaging can be linked with the position of the sensor of the system 50A relative to the patient 70. Accordingly, as the system 50A is moved with respect to the patient 70, the objects of virtual anatomy displayed can also be modified to correspond with the position of the system 50A.

The display 30A therefore displays objects of virtual anatomy that corresponds with internal portions of the patient 70 disposed below the system 50A and the sensor thereof. In an embodiment, the imaging can be performed prior to the sensor being implemented and saved to the system 50A. In an embodiment, the images can be constantly updated to the display 30A to reflect a dynamic image of the internal portions of the patient 70 as the catheter 72 is advanced. In an embodiment, the system 50A can further include one or more fiduciary point(s) 230 disposed on the patient 70. Accordingly, the system 50A can use the fiduciary point 230 to determine the location of the sensor of the system 50A relative to the patient 70. The system 50A can then anchor the images, information, three-dimensional renderings of the virtual anatomy, and the like, to the patient 70.

In an embodiment, the display 30A can be a touch screen display and include various buttons 226 displayed thereon for controlling the functionality of the system 10. For example, buttons included on the probe 40, can also be included on the system 50A and can be used to immediately call up a desired mode to the display 30A by the clinician to assist in the placement procedure. In an embodiment, as shown in FIG. 14 the display can further include graphical elements 224 such as symbols, images, icons, or the like, to depict a location, orientation, distance, depth, combinations thereof, or the like when the medical device is not immediately below the sensor 50. It will be appreciated that the display 30A can include light-emitting diode (LED) displays, electroluminescent (ELD) displays, E-ink displays, electronic paper displays, plasma displays, liquid crystal displays (LCD), Organic light-emitting diode displays (OLED), Digital Light Processing display (DLP), and the like without departing from the spirit of the invention.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A method of tracking a medical device, comprising:
positioning a housing of a sensor on a target area of a patient, a lower surface of the housing designed to contact a skin surface of the patient and remain stationary while the medical device is moved within the patient from a skin insertion site to the target area, the sensor including an LED array of one or more LED lights;
inserting the medical device in a vasculature of the patient; and
indicating a proximity of the medical device to the sensor by a first LED light of the LED array projecting an arrow symbol onto a surface of the patient, the arrow symbol indicating the proximity of the medical device to the sensor.

2. The method of claim 1, wherein the proximity of the medical device to the sensor includes one or both of a distance and a depth of the medical device in three-dimensional space.

3. The method of claim 1, wherein the one or more LED lights of the LED array displays more than one color, the more than one color indicating the proximity of the medical device relative to the sensor.

4. The method of claim 1, wherein one of the first LED light or a second LED light of the LED array illuminate when the medical device is disposed directly thereunder.

5. The method of claim 1, further including projecting one of an alphanumeric symbol, an image, or an icon.

6. The method of claim 5, wherein one of the arrow symbol, alphanumeric symbol, image, or icon, projected onto the surface of the patient indicates one or more of a location, a direction, a distance, or a depth of the medical device relative to the sensor.

7. The method of claim 1, wherein the LED array is a display configured to provide an image of the medical device when the medical device is disposed below the sensor.

* * * * *